United States Patent [19]
Zdarsky

[11] Patent Number: 5,516,287
[45] Date of Patent: May 14, 1996

[54] ROOT-CANAL PREPARING INSTRUMENT

[75] Inventor: Edward Zdarsky, Palm Beach, Fla.

[73] Assignee: Vereinigte Dentalwerke Antaeos Beutelrock Zipperer Zdarsky Ehrler GmbH & Co. KG, Munich, Germany

[21] Appl. No.: 243,481

[22] Filed: May 13, 1994

[51] Int. Cl.[6] .................................................. A61C 5/02
[52] U.S. Cl. ........................ 433/102; 433/141; 433/224
[58] Field of Search ................................. 433/102, 141, 433/224, 143, 147, 75, 144, 164; 40/913; 16/110 R, DIG. 12, DIG. 18, DIG. 19; 81/489, 177.1

[56]          References Cited

U.S. PATENT DOCUMENTS 2,603,999   7/1952  Boutte ................................. 81/177.1
3,185,001   5/1965  Viator ................................. 81/177.1
5,054,154  10/1991  Schiffer et al. ...................... 15/167.1
5,339,482   8/1994  Desimone et al. .................... 15/167.1

FOREIGN PATENT DOCUMENTS 0205937  12/1986  European Pat. Off. ............. 433/102
4219253  12/1993  Germany ............................. 81/489

Primary Examiner—Cary E. O'Connor
Attorney, Agent, or Firm—Lowe, Price, Leblanc & Becker

[57]          ABSTRACT

A dental root-canal preparation instrument includes a grip and a tool contained therein. The grip has a body fitted at its periphery with axially spaced zones preferably in the form of rings projecting above the periphery of the body. The rings are made of silicone rubber to increase grippability when manually grasping the preparation instrument.

11 Claims, 1 Drawing Sheet

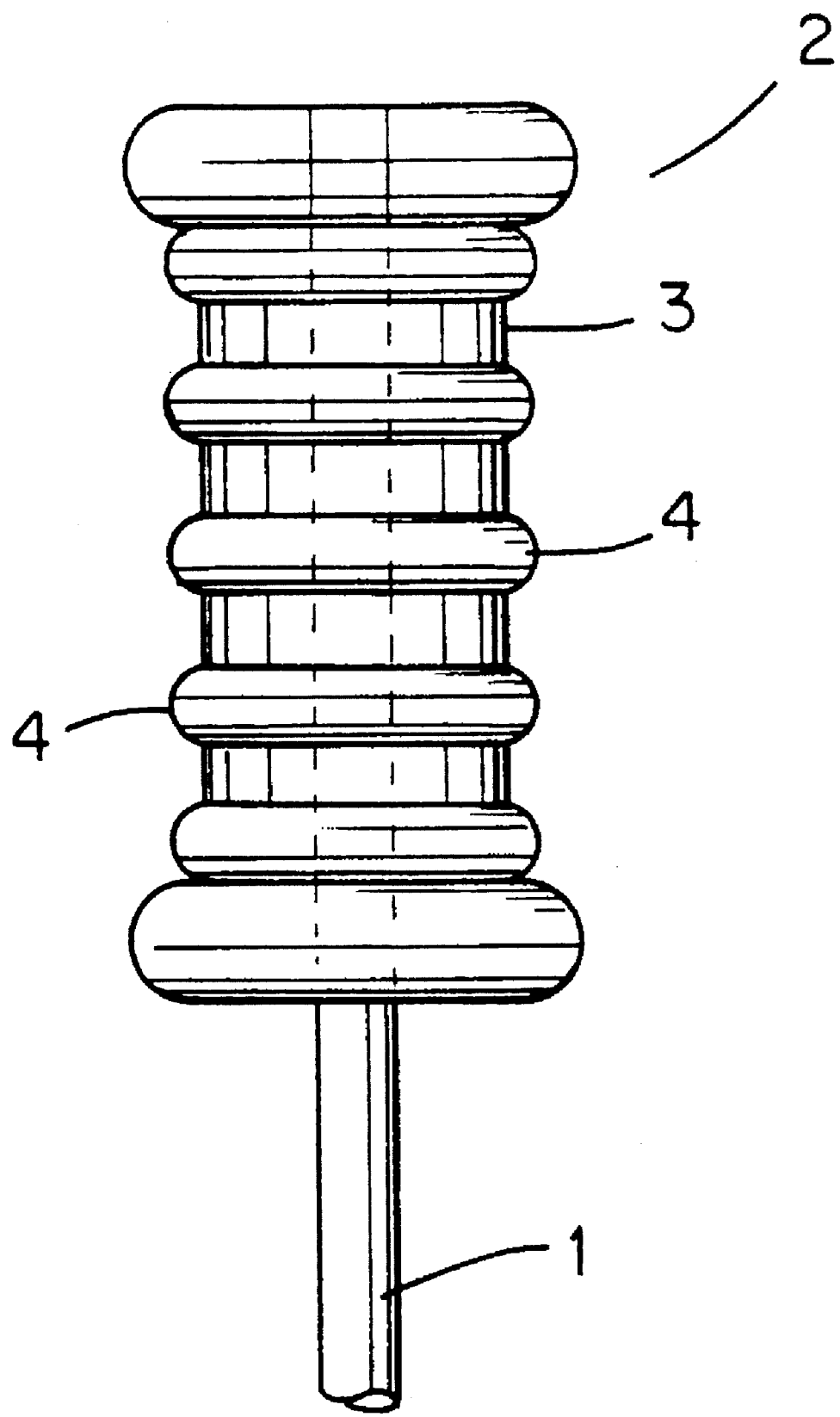

ROOT-CANAL PREPARING INSTRUMENT

TECHNICAL FIELD

The invention concerns a dental root-canal preparing instrument with a grip and a tool contained therein.

BACKGROUND ART

Root-canal preparing instruments are commercially available for instance in the form of root-canal drill bits, files or rasps and serve to widen and clean root canals.

For that purpose the root-canal preparing instrument with the desired dimensions is selected from a set of such instruments, by manually grasping the desired one by its grip.

The grip of a conventional root-canal preparing instrument is made of solid plastic, such as polyphenylene sulfide, which is resistant to chemicals and heat to facilitate required sterilization after use. Unfortunately, the gripping reliability needed for sure handling is lacking.

SUMMARY OF THE INVENTION

An object invention is to create a root-canal preparing instrument of the having improved grippability.

This problem is solved by the invention in that the grip includes a body fitted with a plastic-elastic material in axially spaced zones at its periphery.

Preferably the plastic-elastic material shall be silicone rubber and the plastic-elastic zones are axially spaced projecting rings on the exterior of the grip body.

The grip of the root-canal preparing instrument of the invention may be formed by the grip body being directly enclosed by injection-molding at the axially spaced zones by the plastic-elastic material, or by the grip being a two-component injection molding made from the material of the grip body and of the plastic-elastic material.

The desired gripping reliability is provided by the invention because of the zones at the periphery of the grip body consisting of a plastic-elastic material of higher adhesion and grippability, without thereby degrading the required strength and resistance of the grip required to transmit torques from this grip to the tool.

BRIEF DESCRIPTION OF THE DRAWING

An especially preferred embodiment of the invention is elucidated below in relation to the attached drawing.

The single FIGURE shows a sideview of the grip of the embodiment of the preparing instrument of the invention.

DETAILED DESCRIPTION

As shown by the drawing, a dental root-canal preparing instrument comprises a grip 2, within which is mounted the shank of a tool 1.

The required moments and in particular torques are transmitted by the grip 2 to the tool 1 when the preparation instrument is being operated.

The grip 2 includes of a body 3 made of a plastic in the manner of conventional root-canal preparation instruments, for instance a plastic of high thermal resistance such as polyphenylenesulfide. This material has worked out best in recent years regarding dental equipment.

As further shown by the drawing, projecting and preferably annular zones 4 which are axially spaced and consist of another material are present at the outside of the body 3 of the grip 2. The annular zones 4 so project from the outside of the body 3 that the overall body is tinted.

The material of the zones is plastic-elastic, for instance silicone rubber, which also must be resistant to chemicals and heat with respect to sterilization, just as the body of the grip must be. However the material of the zones 4 may be substantially softer than that of the grip body 3, as a result of which it evinces higher adhesion and grippability when the hand seizes this grip 2. In this manner the grip 2 consisting of a hard and less grippable material may be endowed with high grippability.

The annular zones 4 may consist of colored plastics and always of a color corresponding to the color coding of instrument size.

The grip 2 may be formed by injection-molding the material of the zones 3 directly around the body 3 or by being formed as a whole as a two-component injection-molding from the material of the body 3 and the material of the zones 4 or by double casting using two diametrically opposite channels parallel to the grip axis.

The annular zones 4 consisting of a soft-plastic material can be implemented by pouring, using a channel running parallel to the body axis in the outer surface of the body 3, or by double-pouring, using two diametrically opposite channel parallel to the body axis.

I claim:

1. A dental root-canal preparing instrument comprising a grip made from a plastic material and a tool contained therein, said grip including a body and portions protruding radially from the body in axially spaced locations from each other over at least a major portion of the body, wherein the body and said portions are made from different materials, said portions made of a plastic elastic material.

2. The instrument defined in claim 1, wherein the plastic-elastic material is a silicone rubber.

3. The instrument defined in claim 1, wherein the axially spaced zones assume the shape of rings projecting from the periphery of the body of the grip.

4. The instrument defined in claim 3, wherein the body of the grip is directly enclosed by plastic-elastic injection molding at the axially spaced zones.

5. The instrument defined in claim 1, wherein the body of the grip is directly enclosed by plastic-elastic injection molding at the axially spaced zones.

6. The instrument defined in claim 1, wherein the grip is a two-component injection molding consisting of the material of the body and of the material of the axially spaced zones.

7. The instrument of claim 1, wherein said portions are made of softer material than a material from which said body is formed.

8. The instrument of claim 1, wherein said portions are of a different color from the body.

9. The instrument of claim 1, wherein said portions extend around an entire periphery of the body.

10. The instrument of claim 9, wherein said entire periphery is a circumference.

11. The instrument of claim 1, wherein said portions extend over the entire length of the body.-IN

* * * * *